United States Patent
King et al.

(10) Patent No.: US 7,819,925 B2
(45) Date of Patent: Oct. 26, 2010

(54) COMPOSITE PROSTHETIC BEARING HAVING A CROSSLINKED ARTICULATING SURFACE AND METHOD FOR MAKING THE SAME

(75) Inventors: Richard King, Warsaw, IN (US); Donald E. McNulty, Warsaw, IN (US); Todd S. Smith, Fort Wayne, IN (US)

(73) Assignee: DePuy Products, Inc., Warsaw, IN (US)

( * ) Notice: Subject to any disclaimer, the term of this patent is extended or adjusted under 35 U.S.C. 154(b) by 0 days.

(21) Appl. No.: 10/058,495

(22) Filed: Jan. 28, 2002

(65) Prior Publication Data

US 2003/0144741 A1      Jul. 31, 2003

(51) Int. Cl.
    *A61F 2/28* (2006.01)
(52) U.S. Cl. .................................. 623/23.58
(58) Field of Classification Search ............. 623/19.11, 623/19.13, 20.22, 20.23, 20.33, 21.13, 21.16, 623/22.16, 22.17, 22.18, 22.24, 23.59, 23.58, 623/23.4, 23.43
See application file for complete search history.

(56) References Cited

U.S. PATENT DOCUMENTS

| | | | |
|---|---|---|---|
| 2,948,666 A | 11/1956 | Lawton | |
| 3,297,641 A | 1/1967 | Werber et al. | |
| 3,352,818 A | 11/1967 | Meyer et al. | |
| 3,646,155 A | 2/1972 | Scott | ........................... 260/827 |
| 3,671,477 A | 6/1972 | Nesbitt | ....................... 524/424 |
| 3,758,273 A | 9/1973 | Johnston et al. | |
| 3,944,536 A | 3/1976 | Lupton et al. | |
| 4,055,862 A | 11/1977 | Farling | |
| 4,138,382 A | 2/1979 | Polmanteer | .................. 523/113 |

(Continued)

FOREIGN PATENT DOCUMENTS

BE       A-1001574       12/1989

(Continued)

OTHER PUBLICATIONS

"Poly Two Carbon-Polyethylene Composite-A Carbon Fiber Reinforced Molded Ultra-High Molecular Weight Polyethylene", Technical Report, Zimmer (a Bristol-Myers Squibb Company), Warsaw (1977).

(Continued)

*Primary Examiner*—Anu Ramana
(74) *Attorney, Agent, or Firm*—Barnes & Thornburg LLP (57) ABSTRACT

An implantable prosthetic bearing is constructed of a composite material having a first layer and second layer. The first layer has an articulating surface defined therein, whereas the second layer has a engaging surface defined therein for engaging either another prosthetic component or the bone itself The first layer of the implantable prosthetic bearing is constructed of crosslinked polymer such as Ultra-High Molecular Weight Polyethylene, whereas the second layer of the implantable prosthetic bearing is constructed of polymer such as Ultra-High Molecular Weight Polyethylene that is either non-crosslinked or crosslinked to a lesser degree than the first layer. In such a manner, the first layer possesses mechanical properties which are advantageous in regard to the articulating surface (e.g., enhanced wear and oxidation resistance), whereas the second layer possesses mechanical properties which are advantageous in regard to the engaging surface (e.g., high ductility, toughness, and creep resistance). A method of making a prosthetic bearing is also disclosed.

13 Claims, 3 Drawing Sheets

U.S. PATENT DOCUMENTS

| | | | |
|---|---|---|---|
| 4,281,420 A | 8/1981 | Raab | |
| 4,366,618 A | 1/1983 | Lakes | |
| 4,390,666 A | 6/1983 | Moriguchi | 525/194 |
| 4,483,333 A | 11/1984 | Wartman | 128/90 |
| 4,518,552 A | 5/1985 | Matsuo et al. | 264/126 |
| 4,539,374 A | 9/1985 | Fenton et al. | 525/240 |
| 4,582,656 A | 4/1986 | Hoffmann | |
| 4,586,995 A | 5/1986 | Randall et al. | |
| 4,655,769 A | 4/1987 | Zachariades | |
| 4,668,527 A | 5/1987 | Fujita et al. | 427/35 |
| 4,743,493 A | 5/1988 | Sioshansi et al. | |
| 4,747,990 A | 5/1988 | Gaussens et al. | |
| 4,816,517 A | 3/1989 | Wilkus | 524/520 |
| 4,876,049 A | 10/1989 | Aoyama et al. | |
| 4,888,369 A | 12/1989 | Moore, Jr. | 524/100 |
| 4,902,460 A | 2/1990 | Yagi | 264/83 |
| 4,944,974 A | 7/1990 | Zachariades | |
| 5,014,494 A | 5/1991 | George | |
| 5,024,670 A | 6/1991 | Smith et al. | |
| 5,037,928 A | 8/1991 | Li et al. | |
| 5,106,545 A | 4/1992 | Warren | |
| 5,130,376 A | 7/1992 | Shih | 525/240 |
| 5,133,757 A | 7/1992 | Sioshansi et al. | 623/18 |
| 5,137,688 A | 8/1992 | DeRudder | |
| 5,153,039 A | 10/1992 | Porter et al. | |
| 5,160,464 A | 11/1992 | Ward et al. | |
| 5,160,472 A | 11/1992 | Zachariades | |
| 5,180,394 A | 1/1993 | Davidson | 623/18 |
| 5,192,323 A | 3/1993 | Shetty et al. | 623/16 |
| 5,200,439 A | 4/1993 | Asanuma | |
| 5,210,130 A | 5/1993 | Howard, Jr. | |
| 5,236,563 A | 8/1993 | Loh | 204/165 |
| 5,356,998 A | 10/1994 | Hobes | |
| 5,407,623 A | 4/1995 | Zachariades et al. | |
| 5,414,049 A | 5/1995 | Sun et al. | 525/333.7 |
| 5,439,949 A | 8/1995 | Lucas et al. | |
| 5,449,745 A | 9/1995 | Sun et al. | 528/483 |
| 5,466,530 A | 11/1995 | England et al. | |
| 5,478,906 A | 12/1995 | Howard, Jr. | |
| 5,480,683 A | 1/1996 | Chabrol et al. | |
| 5,495,319 A | 2/1996 | DeNicola | 526/352 |
| 5,515,590 A | 5/1996 | Pienkowski | |
| 5,543,471 A | 8/1996 | Sun et al. | |
| 5,549,698 A | 8/1996 | Averill et al. | |
| 5,549,700 A | 8/1996 | Graham et al. | |
| 5,577,368 A * | 11/1996 | Hamilton et al. | 53/432 |
| 5,593,719 A | 1/1997 | Deamaley et al. | 427/2.26 |
| 5,607,518 A | 3/1997 | Hoffman et al. | |
| 5,609,638 A | 3/1997 | Price et al. | 623/18 |
| 5,645,594 A | 7/1997 | Devanathan et al. | |
| 5,645,882 A | 7/1997 | Llanos | 427/2.24 |
| 5,650,485 A | 7/1997 | Sun et al. | |
| 5,674,293 A | 10/1997 | Armini et al. | 623/16 |
| 5,702,448 A | 12/1997 | Buechel et al. | 623/16 |
| 5,702,456 A | 12/1997 | Pienkowski | 623/18 |
| 5,709,020 A | 1/1998 | Pienkowski et al. | |
| 5,728,748 A | 3/1998 | Sun et al. | |
| 5,753,182 A | 5/1998 | Higgins | |
| 5,876,453 A | 3/1999 | Beaty | 623/16 |
| 5,879,388 A | 3/1999 | Pienkowski et al. | 623/18 |
| 5,879,400 A | 3/1999 | Merrill et al. | 623/22 |
| 5,879,407 A | 3/1999 | Waggener | 623/22 |
| 6,017,975 A | 1/2000 | Saum et al. | |
| 6,087,553 A | 7/2000 | Cohen et al. | |
| 6,143,232 A | 11/2000 | Rohr | |
| 6,165,220 A * | 12/2000 | McKellop et al. | 128/898 |
| 6,168,626 B1 * | 1/2001 | Hyon et al. | 623/18.11 |
| 6,203,844 B1 * | 3/2001 | Park | 427/2.26 |
| 6,228,900 B1 * | 5/2001 | Shen et al. | 522/153 |
| 6,245,276 B1 | 6/2001 | McNulty et al. | |
| 6,281,264 B1 * | 8/2001 | Salovey et al. | 523/115 |
| 6,316,158 B1 | 11/2001 | Saum et al. | |
| 6,365,089 B1 * | 4/2002 | Krebs et al. | 264/485 |
| 6,414,086 B1 * | 7/2002 | Wang et al. | 525/191 |
| 6,494,917 B1 * | 12/2002 | McKellop et al. | 623/23.58 |
| 6,547,828 B2 * | 4/2003 | Scott et al. | 623/66.1 |
| 6,641,617 B1 * | 11/2003 | Merrill et al. | 623/23.58 |
| 6,652,943 B2 * | 11/2003 | Tukachinsky et al. | 428/36.91 |
| 6,794,423 B1 * | 9/2004 | Li | 522/157 |
| 6,849,224 B2 * | 2/2005 | Wang et al. | 264/478 |
| 2001/0026033 A1 | 10/2001 | Smith et al. | |

FOREIGN PATENT DOCUMENTS

| | | |
|---|---|---|
| EP | 0 169 259 | 7/1984 |
| EP | 0 373 800 A1 | 6/1990 |
| EP | 0722973 A1 | 7/1996 |
| EP | 0729981 A1 | 9/1996 |
| EP | 0 737481 A1 | 10/1996 |
| EP | 0 963 824 A2 | 12/1999 |
| EP | 1072277 A1 * | 1/2001 |
| EP | 0 963 824 A3 | 9/2001 |
| EP | 1 421 918 | 11/2003 |
| JP | 58-157830 A | 9/1983 |
| JP | A-59 168 050 | 9/1984 |
| JP | A-62 243 634 | 1/1987 |
| JP | 04-198242 | 7/1992 |
| JP | A-04 185651 | 7/1992 |
| JP | 09 12 22 22 | 5/1997 |
| WO | WO 93/10953 | 6/1993 |
| WO | WO 95/21212 | 8/1995 |
| WO | WO 96/09330 | 3/1996 |
| WO | WO 97/29793 | 8/1997 |
| WO | WO 98/01085 | 1/1998 |
| WO | WO 98/14223 | 4/1998 |

OTHER PUBLICATIONS

Atkinson, J.R. et al., "Silane cross-linked polyethylene for prosthetic applications. Part I. Certain physical and mechanical properties related to the nature of the material", Biomaterials, 4:267 (1983).

Atkinson, J.R. et al., "Silane cross-linked polyethylene for prosthetic applications. Part II. Creep and wear behavior and a preliminary moulding test", Biomaterials, 5:326 (1984).

Bartel, D.L. et al., "The Effect of Comformity, Thickness, and Material on Stresses in Ultra-High Molecular Weight Components for Total Hip Replacement", J. Bone & Joint Surgery, 68-A(7):1041 (1986).

Bhateja, S.K., "Radiation-Induced Crystallinity Changes in Pressure-Crystallized Ultra-High Molecular Weight Polyethylene", J. Macromol. Sci. Phys., B22(1): 159 (1983).

Bhateja, S.K. et al., "Radiation-Induced Crystallinity Changes in Linear Polyethylene", J. Polym. Sci. Polym. Phys. Ed., 21: 523 (1983).

Bhateja, S.K. et al., "Radiation-Induced Crystallinity Changes in Polyethylene Blends", J. Mater. Sci., 20: 2839 (1985).

Birkinshaw, C. et al., "The Melting Behavior of Irradiated Polymers", Thermochimica Acta, 117: 365 (1987).

Bloebaum, R.D. et al., "Investigation of Early Surface Delamination Observed in Retrieved Heat-Pressed Tibial Inserts", Clin. Orthop., 269: 120 (1991).

Bremmer, T. et al., "Peroxide Modification of Linear Low-Density Polyethylene: A Comparison of Dialkyl Peroxides", J. Appl. Polym. Sci., 49 : 785 (1993).

Brown, K. J. et al., "The Wear of Ultra-High Molecular Weight Polyethylene with Reference to Its Use in Prostheses", Plastics in Medicine & Surgery Plastics & Rubber Institute, London, 2.1 (1975).

Chen, C.J. et al., "Radiation-Induced crosslinking: II. Effect on the crystalline and amorphous densities of polyethylene", Coll. & Polym. Sci.,269: 469 (1991).

Chen, Y.L. et al., "Photocrosslinking of Polyethylene I. Photoinitiators, Crosslinking Agent, and Reaction Kinetics", J. Polym. Sci., Part A: Polym. Chem. 27: 4051 (1989).

Chen, Y.L. et al., "Photocrosslinking of Polyethylene. II. Properties of Photocrosslinked Polyethylene", J. Polym. Sci., Part A; Polym. Chem., 27: 4077 (1989).

Connelly, G.M. et al., "Fatigue Crack Propagation Behavior of Ultrahigh Molecular Weight Polyethylene", J. Orthop. Res., 2: 119 (1984).

deBoer, A.P. et al., "Polyethylene Networks Crosslinked in Solution: Preparation, Elastic Behavior, and Oriented Crystallization. I. Crosslinking in Solution", J. Polym. Sci., Polym. Phys. Ed., 14: 187 (1976).

deBoer, J. et al., "Crosslinking of Ultra-High Molecular Weight Polyethylene in the Melt by Means of 2,5-dimethyl-2,5-bis (tert-butyldioxy)-3-hexyne", Makromol. Chem. Rapid Commun., 2: 749 (1981).

deBoer, J. et al., "Crosslinking of Ultra-High Molecular Weight Polyethylene in the Melt by Means of 2,5-dimethyl-2,5-bis (tert-butyldioxy)-3-hexyne: 2. Crystallization Behavior and Mechanical Properties", Polymer, 23: 1944 (1982).

deBoer, J. et al., "Crosslinking of Ultra-High Molecular Weight Polyethylene in the Oriented State with Dicumylperoxide", Polymer, 25: 513 (1984).

Dijkstra, D.J. et al., "Cross-linking of ultra-high molecular weight polyethylene in the melt by means of electron bean irradiation", Polymer, 30: 866 (1989).

Ding Z.Y. et al., "Model Filled Polymers. VI. Determination of the Crosslink Density of Polymeric Beads by Swelling," J. Polym. Sci., Part B: Poly. Phys., 29: 1035 (1991).

Eyerer, P. et al., "Property changes of UHMW polyethylene hip cup endoprostheses during implantation", J. Biomed. Materials Res., 18: 1137 (1984).

Eyerer, P., "Polyethylene", Concise Encyclopedia of Medical and Dental Implant Materials, Pergamon Press, Oxford, 271 (1990).

Ferris, B.D., "A quantitiative study of the tissue reaction and its relationship to debris production from a joint implant", J. Exp. Path., 71: 367 (1990).

Gielenz G. et al., "Crystalline and supermolecular structures in linear polyethylene irradiated with fast electrons", Colloid & Polymer Sci., 260: 742 (1982).

Grobbelaar, C.J. et al., "The Radiaion improvement of Polyethylene Prosthesis", J. Bone & Joint Surgery, 60-B(3): 370-374 (1978).

Goodman, S. et al., "Polyethylene wear in knee arthroplasty", Acta Orthop. Scand., 63(3): 358 (1992).

Grood, E.S. et al., "Analysis of retrieved implants: Crystallinity changes in ultrahigh molecular weight polyethylene", J. Biomedical Materials Res., 16: 399 (1982).

Huang, D.D. et al., "Cyclic Fatigue Behaviors of UHMWPE and Enhanced UHMWPE", Trans. $38^{th}$ Ann. Mtg., Orthop. Res. Soc., 403 (1992).

Kamel, I. et al., "A Model for Radiation-Induced Changes in Ultrahigh-Molecular-Weight-Polyethylene", J. Polym. Sci., Polym. Phys. Ed., 23:2407 (1985).

Kampouris, E.M. et al., "Benzyl Peroxide as a Crosslinking Agent for Polyethylene", J. Appl. Polym. Sci., 34: 1209 (1987).

Kao, Y.H., "Crystallinity in chemically crosslinked low density polyethylenes: 1 Structural and fusion studies", Polymer, 27: 1669 (1986).

Katq, K. et al., "Structural Changes and Melting Behavior of γ-Irradiated Polyethylene", Japanese J. Appl. Phys., 20: 691 (1981).

Kunert, K.A. et al., "Structural investigation of chemically crosslinked low density polyethylene", Polymer, 22: 1355 (1981).

Kurth, M. et al., "Effects of Radiation Sterilization on UHMW-Polyethylene", Trans. Third World Biomaterials Congress, 589 (1988).

Landy, M.M. et al., "Wear of Ultra-high-molecular-weight Polyethylene Components of 90 Retrieved Knee Prostheses", J. Arthroplasty, Supplement, 3: S73 (1988).

Lem, K. et al., "Rheological Properties of Polyethylenes Modified with Dicumyl Peroxide", J. Appl. Polym. Sci., 27: 1367 (1982).

Li, S. et al., "Characterization and Description of an Enhanced Ultra High Molecular Weight Polyethylene for Orthopaedic Bearing Surfaces", Trans. $16^{th}$ Ann. Soc. Biomaterials Meeting, Charleston, SC, 190 (1990).

Manley, T.R. et al., "The effects of varying peroxide concentration in crosslinked linear polyethylene", Polymer, 12:176 (1971).

McKellop, H. et al., "Friction, Lubrication and Wear of Polyethylene Metal and Polyethylene/Ceramic Hip Prostheses on a Joint Simulator", Fourth World Biomaterials Congress, Berlin, April, 118 (1992).

Minkova, L., "DSC of γ-irradiated ultra-high molecular weight polyethylene and high density polyethylene of normal molecular weight", Colloid & Polymer Sci., 266: 6 (1988).

Minkova, L. et al., "Blends of normal high density and ultra-high molecular weight polyethylene, γ-irradiated at a low dose", Colloid & Polymer Sci., 268: 1018 (1990).

Nagy, E.V. et al., "A Fourier transform infrared technique for the evaluation of polyethylene orthopaedic bearing materials", Trans. $16^{th}$ Ann. Soc. For Biomaterials Meeting, Charleston, SC 109 (1990).

Narkis, M. et al., "Structure and Tensile Behavior of Irradiation-and Peroxide-Crosslinked Polyethylene", J. Macromol. Sci.-Phys., B26(1): 37 (1987).

Nusbaum, H. J. et al., "The Effects of Radiation Sterilization on the Properties of Ultrahigh Molecular Weight Polyethylene", J. Biomed. Materials Res., 13: 557 (1979).

Oonishi, H. et al., "Improvement of Polyethylene by Irradiation in Artificial Joints", Radiat, Phys. Chem., 39: 495 (1992).

Oonishi, H. et al., "In Vivo and In Vitro Wear Behavior on Weightbearing Surfaces of Polyethylene Sockets Improved by Irradiation in Total Hip Prostheses", Surface Modification Technologies V, 101-115 (1992), Sudarsahn T.S. et al., ed. The Institute of Materials.

Painter, P.C., et al., "The Theory of Vibrational Spectroscopy and its Application to Polymeric Materials", Ed. John Wiley & Sons, New York, U.S.A., (1982).

Paul, J. P., "Forces Transmitted by Joints in the Human Body", Proc. Instn. Mech. Engrs. 181, Part 3J, Paper 8 (1966).

Qu, B.J. et al., "Photocross-linking of Low Density Polyethylene. I Kinetics and Reaction Parameters", J. Appl. Polym. Sci., 48: 701 (1993).

Qu, B.J. et al., "Photocross-linking of Low Density Polyethylene. II Structure and Morphology", J. Appl. Polym. Sci., 48: 711 (1993).

Rimnac, C.M. et al., "Chemical and Mechanical Degradation of UHMWPE: Report of the Development of an In vitro Test", J. Appl. Biomaterials, 5:17 (1994).

Rimnac, C.M. et al., "Observations of Surface Damage and Degradation on Retrieved PCA Knee Implants", Trans. $38^{th}$ Ann. Orthopaedic Res. Society, Washington, D.C., 330 (1992).

Rimnac, C.M. et al., "Post-Irradiation Aging of Ultra-High Molecular Weight Polyethylene", J. Bone & Joint Surgery, 76-A(7): 1052 (1994).

Roe, R. et al., "Effect of radiation sterilization and aging on ultrahigh molecular weight polyethylene", J. Biomed. Mat. Res., 15: 209 (1981).

Rose, R.M. et al., "On the True Wear Rate of Ultra-High Molecular Weight Polyethylene in the Total Hip Prosthesis", J. Bone & Joint Surgery, 62A(4): 537(1980).

Rose, R.M. et al., "Exploratory Investigations in the Structure Dependence of the Wear Resistance of Polyethylene", Wear, 77:89 (1982).

Rostoker, W. et al., "The Appearances of Wear on Polyethylene—A Comparison of in vivo and in vitro Wear Surfaces", J. Biomed. Materials Res., 12:317 (1978).

Seedhom, B.B. et al., "Wear of Solid Phase Formed High Density Polyethylene in Relation to the Life of Artificial Hips and Knees", Wear, 24: 35 (1973).

Shen, C. et al., "The Friction and Wear Behavior of Irradiated Very High Molecular Weight Polyethylene", Wear, 30:349 (1974).

Shinde, A. et al., "Irradiation of Ultrahigh-Molecular-Weight Polyethylene", J. Polym. Sci., Polym. Phys. Ed., 23: 1681 (1985).

Spruiell, J.E. et al., "Methods of Experimental Physics", L. Marton & C. Marton, Eds., vol. 16, Part B Academic Press, New York (1980).

Streicher, R.M., "Ionizing irradiation for sterilization and modification of high molecular weight polyethylenes" Plastics & Rubber Processing & Applications, 10: 221 (1988).

Streicher, R.M., "Investigation on Sterilization and Modification of High Molecular Weight Polyethylenes by Ionizing Irradiation", Beta-gamma, 1/89:34-43.

Swanson, S.A.V. et al., "Chapter 3, Friction, Lubrication and Wear", The Scientific Basis of Joint Replacement, Pittman Medical Publishing Co., Ltd. (1977).

Wang, X. et al., "Melting of Ultrahigh Molecular Weight Polyethylene", J. App. Polymer Sci., 34:593 (1987).

Wright, T.M. et al., "The effect of carbon fiber reinforcement on contact area, contact pressure, and time-dependent deformation in polyethylene tibial components", J. Biomed. Materials Res., 15:719 (1981).

Zachariades, A.E., "A New Class of UHMWPE Orthopaedic Prosthetic Devices with Enhanced Mechanical Properties", Trans. Fourth World Biomaterials Congress, Berlin 623 (1992).

Zhao, Y. et al., "Effect of Irradiation on Crystallinity and Mechanical Properties of Ultrahigh Molecular Weight Polyethylene", J. Appl. Polym. Sci., 50:1797 (1993).

"News You Can Use", vol. II, No. 2 (May 1996).

"For the Tough Jobs: 1900 UHMW Polymer", Himont, Inc. (1988).

"Abrasion-Resistant 1900 UHMW Polymer", Hercules, Inc. (1979).

"Technical Information: 1900 Ultrahigh Molecular Weight Polymer, General Information and Applications", Bulletin JPE-101A, Hercules, U.S.A., Inc., (1989).

"Technical Information: 1900 Ultrahigh Molecular Weight Polymer, Nuclear Radiation Effects", Bulletin HPE-111, Himont U.S.A., Inc. (1985).

"Technical Information: 1900 Ultrahigh Molecular Weight Polymer, Effect of Polymer Modification", Bulletin HPE-116, Himont U.S.A., Inc. (1987).

"Ultra-High Molecular Weight Polyethylene as Biomaterial in Orthopaedic Surgery", Hogrefe & Huber Publishers.

Appleby, R.W. et al., "Post-gamma irradiation cross-linking of polyethylene tape by acetylene treatment", J. Material Sci., 29: 227-231 (1994).

Higgins, J.C. et al., "Evaluation of Free Radical Reduction Treatments for UHMWPE", Proceedings of the 42$^{nd}$ Annual Mtg., Orthopaedic Res. Soc., Feb. 19-22:485(1996).

Jasty, M. et al., "Marked Improvement in the Wear Resistance of a New Form of UHMPWE in a Physiologic Hip Simulator", Trans. 43$^{rd}$ Ann. Mtg., Orthopaedic Research Soc., San Francisco, CA, Feb. 9-13:785(1997).

Jasty, M. et al., "Marked Improvement in the Wear Resistance of a New Form of UHMPWE in a Physiologic Hip Simulator", Trans. Soc. Biomaterials, vol. XX, p. 71, 23$^{rd}$ Ann. Mtg. Soc. for Biomaterials. New Orleans, Louisiana, U.S.A., Apr. 30-May 4:157 (1997).

Streicher, Influence of Ionizing Irradiation in Air and Nitrogen for Sterilization of Surgical Grade Polyethylene for Implants, Radiat. Phys. Chem., vol. 31, Nos. 4-6: 693-698 (1988).

Pleiss et al., "The Improvement of Polyethylene Prostheses Through Radiation Crosslinking", Radiat.. Phys. Chem., 9: 647-652 (1977).

Streicher, "The Behavior of UHMW-PE when Subjected to Sterilization by Ionizing Radiation", Ultra-High Molecular Weight Polyethylene as Biomaterial in Orthopedic Surgery, 66-73 (1990).

Saunders, C. et al., "Radiation Effects on Microorganisms and Polymers for Medical Products", Medical Device & Diagnostic Industry, 222:89-22 (1993).

Kang et al., "The Radiation Chemistry of Polyethylene IX. Temperature Coefficient of Cross-linking and Other Effects", J. Amer. Chem. Society, 89(9): 1980-1986 (1967).

Rose et al., "Radiation Sterilization and the Wear Rate of Polyethylene", J. Orthopaedic Res. Society, 2(4): 393-400 (1984).

Oonishi, H. et al., "Super Low Wear Cross-Linked UHMWPE by Heavy High-Dose Gamma Radiation", WPOA 2$^{nd}$ Congress of Hip Section, 61 (1996).

Jahan et al., "Combined chemical and mechanical effects on free radicals in UHMWPE joints during implantation", J. Biomed. Material Res., 25: 1005-1016 (1991).

"Standard Practice for Dosimetry in an Electron Bean Facility for Radiation Processing at Energies Between 300 keV and 25 keV", Am. Soc. for Testing & Materials, Designation: E1649-94, 870-888 (1995).

Oonishi, H. et al., "The Low Wear of Cross-Linked Polyethylene Socket in Total Hip Prostheses", Encyclopedic Handbook of Biomaterials & Bioengineering, vol. 2, Marcel Dekker, Inc., 1853-1868 (1995).

Atkinson, J. et al., "The nature of silane cross-linked HDPE is discussed. Creep and wear tests indicate its potential as a possible replacement for high molecular weight polyethylene in prostheses", Polymers in Medicine and Surgery, Conf. Held by Plastics and Rubber Institute and Biological Engineering Soc., UK. Sep, P4/1-P4/9 (1986).

Jones, W. et al., Effect of γ Irradiation on the Friction and Wear of Ultrahigh Molecular Weight Polyethylene, Wear 70: 77-92 (1981).

Gent, A. et al., "Elastic Behavior, Birefringence, and Swelling of Amorphous Polyethylene Networks", J. Polymer Sci. 5: 47-60 (1967).

Zoepfl, F. et al., "Differential Scanning Calorimetry Studies of Irradiated Polyethylene: I. Melting Temperatures and Fusion Endotherms", J. Polymer Sci. Polym. Chem. Ed., 22: 2017-2032 (1984).

Zoepfl, F. et al., "Differential Scanning Calorimetry Studies of Irradiated Polyethylene: II. The Effect of Oxygen", J. Polymer Sci. Polym. Chem. Ed., 22: 2032-2045 (1984).

Mandelkern, L. et al., "Fusion of Polymer Networks Formed from Linear Polyethylene: Effect of Intermolecular Order", contribution from the General Electric Research Laboratory and from the Polymer Structure Section, National Bureau of Standards 82: 46-53 (1960).

Muratoglu, O.K. et al., "A Comparison of 5 Different Types of Highly Crosslinked UHMWPES: Physical Properties and Wear Behavior", 45$^{th}$ Annual Meeting, Orthopaedic Research Society, Anaheim, CA, Feb. 1-4, 77 (1999).

Muratoglu, O.K. et al., "A Novel Method of Crosslinking UHMWPE to Improve Wear With Little or No Sacrifice on Mechanical Properties", 45$^{th}$ Annual Meeting, Orthopaedic Research Society, Anaheim, CA, Feb. 1-4, 829 (1999).

Muratoglu, O.K. et al., "Electron Beam Cross Linking of UHMWPE At Room Remperature, A Candidate Bearing Material for Total Joint Arthroplasty", 23rd Annual Meeting of the Society for Biomaterials, New Orleans, Lousiana, Apr. 30-May 4, 74 (1997).

Matsubara, K et al., "The Wear Properties of High-Density Polyethylene Irradiated by Gamma Rays", Wear 10: 214 (1967).

McKellop, H. et al., "Increased Wear of UHMW Polyethylene After Gamma Radiation Sterilization", Trans. 26$^{th}$ Ann. ORS, Atlanta, Georgia, Feb. 5-7 (1980).

McKellop, H., "The Effect of Radiation and Ethylene Oxide Sterilization on the Wear of UHMW Polyethylene", 7$^{th}$ European Conference on Biomaterials, Sep. 8-11, (1987).

Shen, F-S. et al., "Irradiation of Chemically Crosslinked Ultrahigh Molecular Weight Polyethylene", J. Polymer Sci.: Part B: Polymer Phys. 34: 1063-1077 (1996).

Oka, M. et al., "Wear-Resistant Properties of Newly Improved UHMWPE", Trans. Fifth World Biomaterials Congress, Toronto, Canada 520, (May 29-Jun. 2, 1996).

Bellare, A. et al., "Deformation, Morphology and Wear Behavior of Polyethylene", Trans. 23$^{rd}$ Ann. Mtg., Soc. Biomaterials, New Orleans, Louisiana, 75 (Apr. 30-May 4, 1997).

Clarke, I.C. et al., "Simulator Wear Study of High-Dose Gamma-Irradiated UHMWPE Cups", Trans. 23$^{rd}$. Ann. Mtg., Soc. Biomaterials, New Orleans, LA, 71, (Apr. 30-May 4, 1997).

Taylor, G. et al., "Stability of $N_2$ Packaged Gamma Irradiated UHMWPE", Trans. 23$^{rd}$ Ann. Mtg., Soc. Biomaterials, New Orleans, LA, 421, (Apr. 30-May 4, 1997).

Taylor, G. et al., "Stability of $N_2$ Packaged Gamma Irradiated UHMWPE", Trans. 43$^{rd}$ Ann. Mtg., Orthopaedic Res. Soc., San Francisco, California, 776 (Feb. 9-13, 1997).

McKellop, H. et al., "The Effect of Sterilization Method, Calcium Stearate and Molecular Weight on Wear of UHMWPE Acetabular Cups", Trans. 23$^{rd}$ Ann. Mtg., Soc. Biomaterials, New Orleans, LA, 43 (Apr. 30-May 4, 1997).

McKellop, H. et al., "Effect of Sterilization Method on the Wear Rate of UHMW Polyethylene Acetabular Cups in a Hip Simulator", Trans. 43$^{rd}$ Ann. Mtg., Orthopaedic Res. Soc. San Francisco, CA, 7, 94-16 Feb. 9-13 (1997).

McKellop, H. et al., "Wear of UHMWPE Acetabular Cups After Gamma Sterilization in Nitrogen, Thermal Stabilization and Artificial Aging", Trans. 23$^{rd}$ Ann. Mtg., Soc. Biomaterials, New Orleans, LA, Apr. 30-May 4, 45 (1997).

Wang, A. et al., "Effect of Radiation Dosage on the Wear of Stabilized UHMWPE Evaluated by Hip and Knee Joint Simulators", Trans. 23$^{rd}$ Ann. Mtg., Soc. Biomaterials, New Orleans, LA, 394 (Apr. 30-May 4, 1997).

Wang, A. et al., "Wear Mechanisms and Wear Testing of Ultra-High Molecular Weight Polyethylene in Total Joint Replacements", Hand-Out for Polyethylene Wear in Orthopaedic Implants Workshop, Trans. 23$^{rd}$ Ann. Mtg., Soc. Biomaterials, New Orleans, LA (Apr. 30-May 4, 1997).

Yu, Y.J. et al., "Oxidation of UHMWPE Acetabular Cups After Sterilization and Wear Testing in a Hip Joint Simulator", Trans. 43$^{rd}$ Ann. Mtg., Orthopaedic Res. Soc. San Francisco, CA, 778 (Feb. 9-13, 1997).

Roe, R. et al., "Effect of Radiation Sterilization and Aging on Ultrahigh Molecular Weight Polyethylene", Journal of Biomedical Materials Research, 15:209-230 (1981).

Li, S. et al., "Chemical Degradation of Polyethylene in Hip and Knee Replacements", 38$^{th}$ Ann. Mtg., Orthopaedic Research Society, Washington, D.C., 41, (Feb. 7-20, 1992).

Kurtz, S.M. et al., "Post-Irradiation Aging and The Stresses in UHMWPE Components for Total Joint Replacement", 40$^{th}$ Ann. Mtg., Orthopaedic Research Society, New Orleans, LA, 584, (Feb. 21-24, 1994).

Lancaster et al., "Friction and Wear", in Jenkins (ed): Polymer Science, 959, 1045, North Holland Publishing Company (1972).

McKellop, H. et al., "Accelerated Aging of Irradiated UHMW Polyethylene for Wear Evaluations", 42$^{nd}$ Annual Meeting, Orthopaedic Research Society, Atlanta, Georgia, 483, (Feb. 19-22, 1996).

Blunn, G.W. et al., "The Effect of Oxidation on the Wear of Untreated and Stabilized UHMWPE", 42$^{nd}$ Annual Meeting, Orthopaedic Research Society, Atlanta, Georgia, 482, (Feb. 19-22, 1996).

"Duration™ Stabilized UHMWPE: an UHMWPE with Superior Wear and Oxidation Resistance; Technical Development and Scientific Evaluation", (Cover sheet and reference page).

Sun, D.C. et al.,"The Origin of the White Band Observed in Direct Compression Molded UHMWPE Inserts", 20$^{th}$ Annual Meeting Society for Biomaterials, 121 (Apr. 5-9, 1994).

Sun, D.C. et al., "On the Origins of a Subsurface Oxidation Maximum and its Relationship to the Performance of UHMWPE Implants", 21$^{st}$ Annual Meeting, Society for Biochemicals, San Francisco, CA, 362: (Mar. 18-22, 1995).

Premnath, V. et al., "Melt Irradiated UHMWPE for Total Hip Replacement: Synthesis & Properties", 43rd Annual Meeting, Orthopedic Res. Soc., San Francisco, CA, 91-16, (Feb. 9-13, 1997).

Muratoglu, O.K. et al., "The Effect of Temperature on Radiation Crosslinking of UHMWPE for Use in Total Hip Arthroplasty", 46$^{th}$ Annual Meeting, Orthopaedic Res. Soc., Orlando, FL, 0547 (Mar. 12-15, 2000).

D.C. Sun, C. Stark, J.H. Dumbleton, "Development of an Accelerated Aging Method for Evaluation of Long-term Irradiation Effects on UHMWPE Implants", Polymer Preprints, vol. 35, No. 2, pp. 969-970, (1994).

A.F. Booth, "Industrial Sterilization Technologies: New and Old Trends Shape Manufacturer Choices", Medical Device & Diagnostic Industry, pp. 64-72, Feb. (1995).

B. Hinsch, "Sterilization Methods for Implants Made of UHMWPE", in Ultra-High Molecular Weight Polyethylene as Biomaterials in Orthopedic Surgery, Toronto: Hogrefe & Huber Publishers, pp. 63-65, (1991).

"Irradiation Effects on Polymers", edited by D.W. Clegg and A.A. Collyer, Elsevier Applied Science, London, (1991).

"Radiation Effects on Polymers", edited by R. L. Clough and S. W. Shalaby, ACS Symposium Series 475, (1991).

P. Eyerer, M. Kurth, H. A. McKellop and T. Mittimeier, "Characterization of UHMWPE hip cups run on joint stimulators", J. Biomedical Materials Research, vol. 21, pp. 275-291, (1987).

A. Wang, D.C. Sun, C.Stark, J.H. Dumbleton, Wear, pp. 181-183:241-249 (1995).

A. Wang, C. Stark, J.H. Dumbleton, "Role of cyclic plastic deformation in the wear of UHMWPE acetabular cups", Journal of Biomedical Materials Research, vol. 29, pp. 619-626, (1995).

A. Edidin et al., "Enhancement of multiaxial mechanical behavior by slot drawing of UHMWPE: a candidate biomaterial for total knee arthroplasty," 46$^{th}$ Annual Mtg., Orthopaedic. Res. Soc., Mar. 12-15, Orlando, FL (2000).

Watkins et al."Fractionation of High Density Polyethylene in Propane by Isothermal Pressure Profiling and Isobaric Temperature Profiling" J. Supercritical Fluids, 4:24-31 (1994).

Fu-Wen Shen, PhD et al., "Surface-Gradient Cross-linked Polyethylene Acetabular Cups—Oxidation Resistance and Wear against Smooth and Rough Femoral Balls", Clinical Orthopaedics and Related Research, No. 430, 2005, pp. 80-88.

Harry McKellop et al., "Development of an Extremely Wear-Resistant Ultra High Molecular Weight Polyethylene for Total Hip Replacements", Journal of Orthopaedic Research, vol. 17, No. 2, 1999, pp. 157-167.

L. Martinotto et al., "Space Charge Behavior of Chemically Cross-linked and Radiation Cross-linked Polyethylene", 2000 Conference on Electrical Insulation and Dielectric Phenomena—IEEE, pp. 109-112.

N. Narkis et al., "Structure and Tensile Behavior of Irradiation- and Peroxide-Crosslinked Polyethylenes", J. Macromol. Sci.—Phys., B26(1), 37-58 (1987).

Peschanskaya, N. et al., "Deformation of Poly(methyl methacrylate) after Exposure to Radiation and Magnetic Fields," Physics of the Solid State, 2002, pp. 1791-1794, vol. 44, No. 9, Russia.

* cited by examiner

Fig. 6

COMPOSITE PROSTHETIC BEARING HAVING A CROSSLINKED ARTICULATING SURFACE AND METHOD FOR MAKING THE SAME

Cross reference is made to U.S. patent application Ser. No. 10/058,508, which issued as U.S. Pat. No. 7,186,364 on Mar. 6, 2007, entitled "Composite Prosthetic Bearing Constructed of Polyethylene and an Ethylene-Acrylate Copolymer and Method for Making the Same" by Richard King, Todd Smith, and Donald McNulty, which is assigned to the same assignee as the present invention and is filed concurrently herewith.

FIELD OF THE INVENTION

The present invention relates generally to a prosthetic bearing, and more particularly to a composite prosthetic bearing having a crosslinked articulating surface and method for making the same.

BACKGROUND OF THE INVENTION

Implantable prosthetic bearings such as acetabular bearings, glenoid bearings, tibial bearings and the like have typically been constructed from polyethylene. Indeed, Ultra-High Molecular Weight Polyethylene (UHMWPE) is generally utilized in the construction of a prosthetic bearing due to its favorable characteristics in relation to the articulating surface of the bearing. Moreover, it has been determined that certain characteristics of UHMWPE may be enhanced by exposing UHMWPE to radiation such as gamma radiation. In particular, exposing UHMWPE to predetermined doses of radiation crosslinks the UHMWPE thereby increasing its wear resistance. As such, heretofore designed prosthetic bearings have been constructed of crosslinked UHMWPE in order to gain the aforedescribed benefits. Techniques for crosslinking, quenching, or otherwise preparing UHMWPE are described in numerous issued U.S. patents, examples of which include U.S. Pat. No. 5,728,748 (and its counterparts) issued to Sun, et al, U.S. Pat. No. 5,879,400 issued to Merrill et al, U.S. Pat. No. 6,017,975 issued to Saum, et al, U.S. Pat. No. 6,242,507 issued to Saum et al, U.S. Pat. No. 6,316,158 issued to Saum et al, U.S. Pat. No. 6,228,900 issued to Shen et al, U.S. Pat. No. 6,245,276 issued to McNulty et al, and U.S. Pat. No. 6,281,264 issued to Salovey et al. The disclosure of each of these U.S. patents is hereby incorporated by reference.

Conventional (i.e. non-crosslinked) UHMWPE also possesses a number of favorable characteristics relating to the construction of a prosthetic bearing. For example, conventional UHMWPE possesses superior ductility, toughness, and creep resistance characteristics relative to other polymers.

A prosthetic bearing is typically designed to include structures or features which perform two primary functions. Firstly, a typical prosthetic bearing design includes an articulating or bearing surface on which either a natural bone structure or a prosthetic component articulates. Secondly, a typical prosthetic bearing design also includes locking features in the form of mechanisms such as pins, tabs, tapered posts, or the like for locking or otherwise securing the bearing to either another component associated with a prosthetic assembly (e.g., a metal shell or tray) or to the bone itself.

As described above, certain polymers may have enhanced characteristics relating to one of these primary functions of the bearing (i.e., the function of providing an articulating surface), whereas other polymers may have enhanced characteristics relating to the other primary function of the bearing (i.e., the function of locking the bearing to another component or to the bone itself). What is needed, however, is a prosthetic bearing which is constructed from polymers which have enhanced characteristics relating to both primary functions of the bearing.

Another challenge associated with implantable prosthetic bearings relates to the construction of bearings which are designed to be secured directly to the bone without the use of a metal shell or tray. For example, prosthetic bearings designed completely of polyethylene may be difficult to affix to the bone with the use of bone cement since most commonly utilized bone cements do not adhere well to polyethylene. As such, a number of bearings have heretofore been designed which attempt to overcome this problem by use of a composite material. For example, a bearing disclosed in U.S. Pat. No. 5,645,594 issued to Devanathan et al includes a first layer of UHMWPE and a second layer of blended UHMWPE and poly methyl methacrylate (PMMA). PMMA is a common component in many types of bone cement. It is disclosed that the PMMA portion of the blend may be either PMMA homopolymers or PMMA copolymers. However, a blend is, by definition, non-homogeneous and is therefore often susceptible to undesirable process and product variations. What is needed therefore is a prosthetic bearing which facilitates enhanced adhesion of the bearing to bone cement when the bearing is being secured directly to bone without the use of an implanted metal shell or tray.

SUMMARY OF THE DISCLOSURE

The present invention provides for an implantable polymer prosthetic bearing constructed of a composite material having a first layer and a second layer. The first layer has an articulating surface defined therein, whereas the second layer has an engaging surface defined therein for engaging either another prosthetic component or the bone itself. In certain embodiments, the first layer of the implantable prosthetic bearing is constructed from a crosslinked polymer such as UHMWPE, whereas the second layer of the implantable prosthetic bearing is constructed from a polymer such as UHMWPE that is either non-crosslinked or crosslinked to a lesser degree than the first layer. In such a manner, the first layer possesses mechanical properties which are advantageous in regard to the articulating surface (e.g., enhanced wear and oxidation resistance), whereas the second layer possesses mechanical properties which are advantageous in regard to the engaging surface (e.g., high ductility, toughness, and creep resistance).

In accordance with one illustrative embodiment, there is provided a method of making an implantable bearing for an orthopaedic prosthesis. The method includes the step of exposing a first polymer layer to a first dose of radiation. The method also includes the step of securing the first polymer layer to a second polymer layer so as to create a composite. The method further includes the step of forming the composite into a predetermined shape of the implantable bearing.

In accordance with another illustrative embodiment, there is provided a method of making an implantable bearing for an orthopaedic prosthesis. The method includes the step of securing a layer of crosslinked polymer to a layer of non-crosslinked polymer so as to create a composite. The method also includes the step of forming the composite into a predetermined shape of the implantable bearing.

In accordance with another illustrative embodiment, there is provided an orthopaedic prosthesis. The prosthesis includes an implantable bearing which is prepared by a process comprising the steps of (i) exposing a first polymer layer to a first dose of radiation, (ii) securing the first polymer layer to a second polymer layer so as to create a composite, and (iii) forming the composite into a predetermined shape.

In accordance with a further illustrative embodiment, there is provided an implantable bearing for an orthopaedic prosthesis. The bearing includes a crosslinked layer of polymer and a non-crosslinked layer of polymer that is secured to the crosslinked layer of polymer.

In accordance with another illustrative embodiment, there is provided an implantable bearing for an orthopaedic prosthesis. The bearing includes a first layer of polymer which is crosslinked to a first degree. The bearing also includes a second layer of polymer which is (i) crosslinked to a second degree that is different than the first degree, and (ii) secured to the first layer of polymer.

The above and other objects, features, and advantages of the present invention will become apparent from the following description and the attached drawings.

DETAILED DESCRIPTION OF THE ILLUSTRATIVE EMBODIMENTS

While the invention is susceptible to various modifications and alternative forms, specific embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

The present invention relates to implantable prosthetic bearings and methods of making the same. What is meant herein by the term "bearing" is an orthopaedic implant prosthetic bearing of any type, condition, shape, or configuration. Such bearings may be utilized in a number of joint replacement or repair procedures such as surgical procedures associated with the hip, shoulders, knees, ankles, knuckles, or any other joint. Referring now to FIGS. 1-6, there is shown a number of implantable prosthetic bearings 10 such as a glenoid bearing 12 for implantation into a glenoid of a patient (not shown), an acetabular bearing 14 for implantation into an acetabulum of a patient (not shown), and a tibial bearing 16 for implantation into a tibia of a patient (not shown). Each of the prosthetic bearings 10 includes an articulating or bearing surface 18 on which a natural or prosthetic component bears. For example, in the case of the glenoid bearing 12, a natural or prosthetic humeral head (not shown) bears on the articulating surface 18. Similarly, in the case of an acetabular bearing 14, a natural or prosthetic femoral head (not shown) bears on the articulating surface 18. Moreover, in the case of the tibial bearing 16, a pair of natural or prosthetic femoral condyles (not shown) bear on the articulating surface 18.

Figure 1:
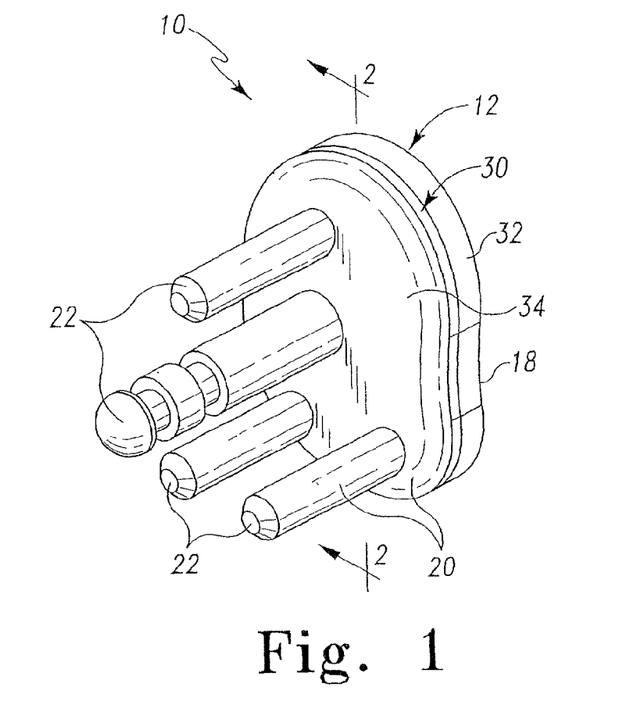
FIG. 1 is a perspective view of an implantable glenoid bearing prosthesis which incorporates the features of the present invention therein.
Figure 2:
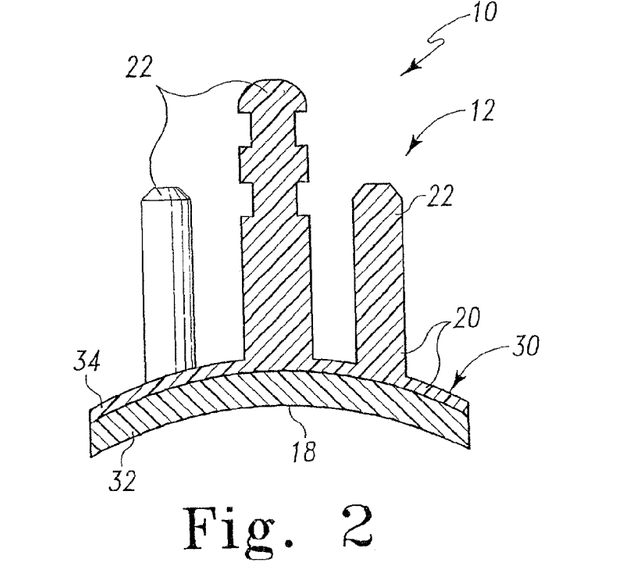
FIG. 2 is a cross sectional view taken along the line 2-2 of FIG. 1.

Each of the prosthetic bearings 10 also includes an engaging surface 20 which has a number of features defined therein for engaging either another prosthetic component or the bone into which the bearing 10 is implanted. For example, in the case of the glenoid bearing 12, a number of pins or pegs 22 may be defined in the engaging surface 20 thereof. The pegs 22 are received into a number of corresponding holes (not shown) formed in the glenoid surface of the patient. The pins 22 may be press fit or held in place with the use of bone cement. Moreover, if the glenoid bearing 12 is utilized in conjunction with an implanted metal shell, the engaging surface 20 of the bearing 12 may be configured with a tapered post (not shown) or the like for securing the glenoid bearing 12 to the shell.

Figure 3:
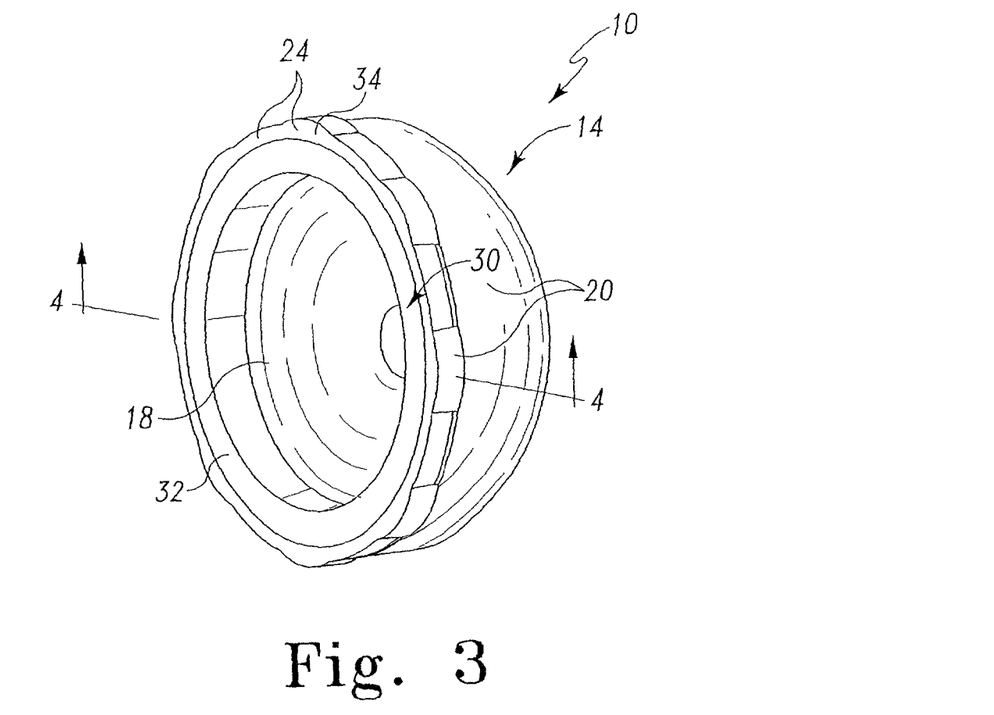
FIG. 3 is a perspective view of an implantable acetabular bearing prosthesis which incorporates the features of the present invention therein.
Figure 4:
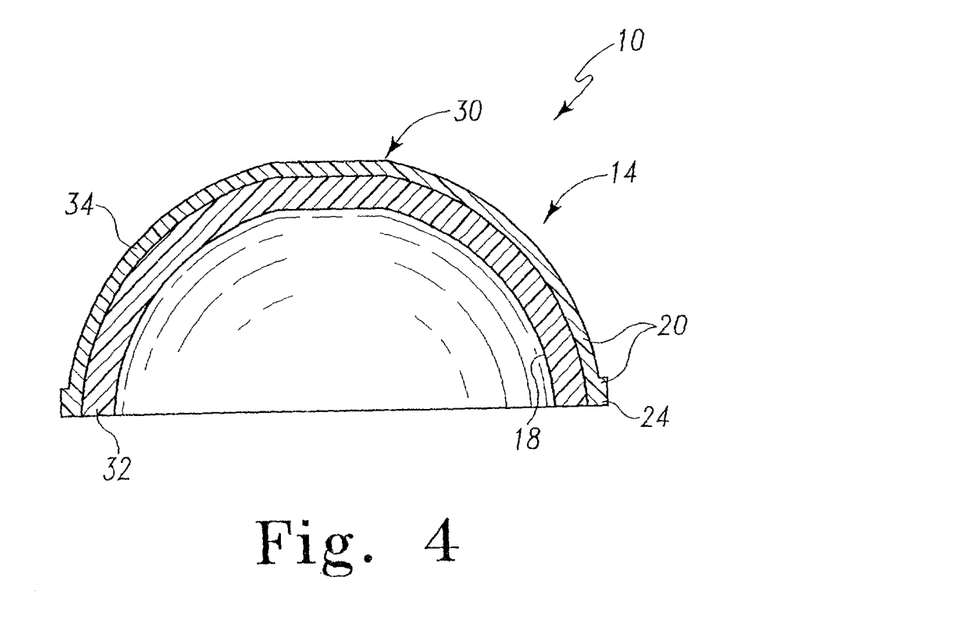
FIG. 4 is a cross sectional view taken along the line 4-4 of FIG. 3.

In the case of the acetabular bearing 14, a number of keying tabs 24 are defined in the engaging surface 20 along the outer annular surface thereof. The keying tabs 24 are received into a number of corresponding keying slots (not shown) defined in an implanted metal acetabular shell (not shown) in order to prevent rotation of the acetabular bearing 14 relative to the implanted shell. In the case of fixation of the acetabular bearing 14 directly to the acetabulum of the patient (i.e., without the use of a metal shell), the engaging surface 20 of the bearing 14 may alternatively be configured with a number of posts or pegs (not shown) which are received into a number of corresponding holes formed in the patient's acetabulum. In such a case, the posts or pegs may be press fit or held in place with the use of bone cement. Moreover, it should be appreciated that the acetabular bearing 14 may be press fit or cemented to the patient's acetabulum without the use of posts or pegs on the engaging surface 20 thereof.

Figure 5:
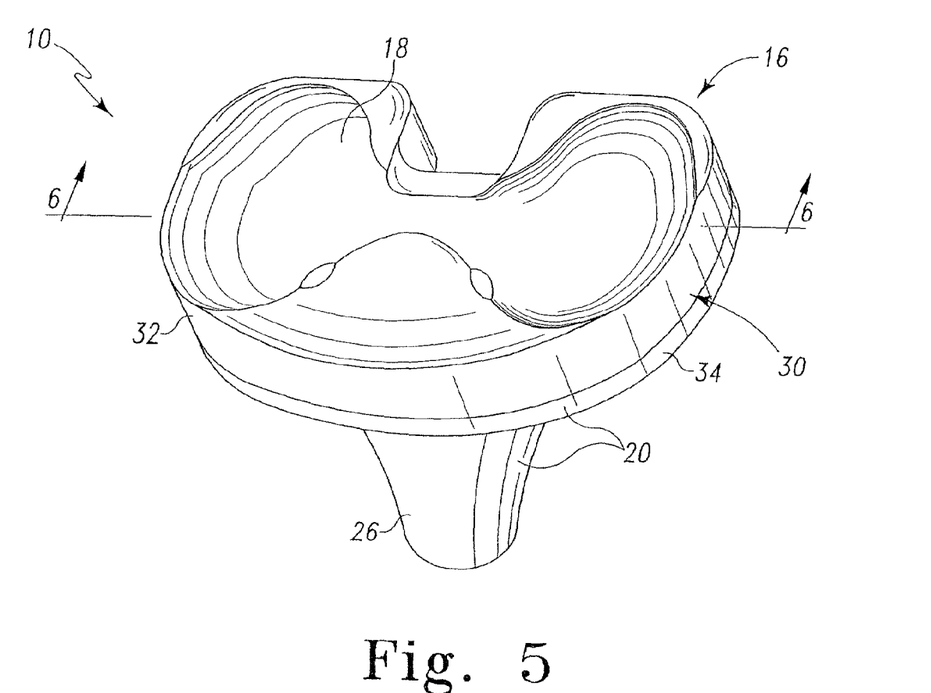
FIG. 5 is a perspective view of an implantable tibial bearing prosthesis which incorporates the features of the present invention therein.
Figure 6:
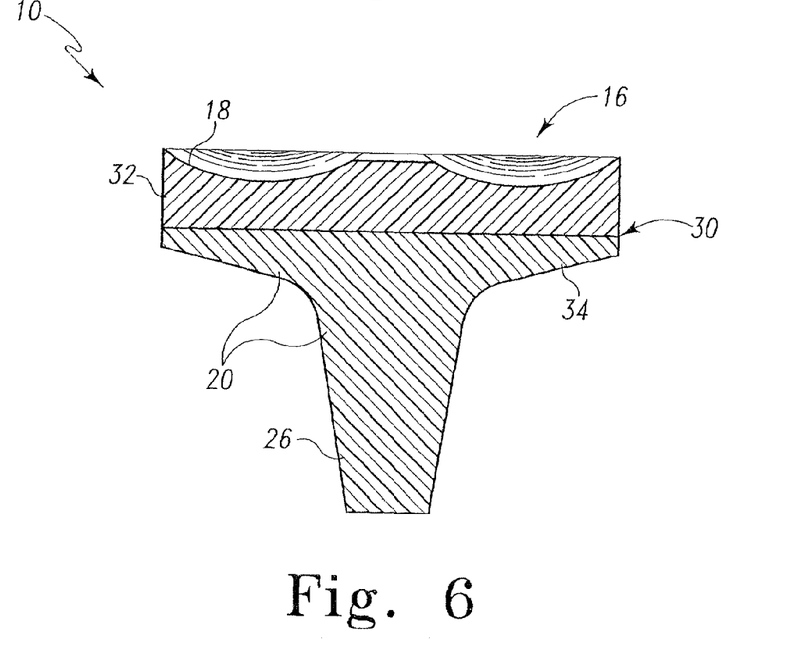
FIG. 6 is a cross sectional view taken along the line 6-6 of FIG. 5.

In the case of the tibial bearing 16, a tapered post 26 is defined in the engaging surface 20 thereof. The tapered post 26 is received into a corresponding tapered bore (not shown) defined in an implanted tibial tray (not shown) of a knee prosthesis (not shown). It should be appreciated that the engaging surface 20 of the tibial bearing 16 may also be configured with features to allow the tibial bearing 16 to be secured directly to the tibia without the use of an implanted tray (e.g., by use of bone cement). Moreover, it should be appreciated that a tibial bearing for use with a tibial tray may also be designed without the use of the post 26.

Each of the bearings 10 is constructed from a laminar composite 30 having a number of layers 32, 34. The first layer 32 of the laminar composite 30 is constructed of a material which possesses mechanical properties favorable for use in the construction of the articulating surface 18 (e.g., enhanced wear and oxidation resistance). The second layer 34, on the other hand, is constructed of a material which possesses mechanical properties favorable for use in the construction of the engaging surface 20 (e.g., enhanced ductility, toughness, and creep resistance). It should be appreciated that the material utilized for construction of the second layer 34 may also be selected based on the fixation type of the bearing 10. In particular, the material utilized for construction of the second layer 34 may also be varied based on, for example, whether the bearing 10 is to be utilized in conjunction with an implanted shell or directly secured to the bone (e.g., by use of bone cement).

It should be appreciated that, as used herein, the term "layer" is not intended to be limited to a "thickness" of material positioned proximate to another similarly dimensioned "thickness" of material, but rather is intended to include numerous structures, configurations, and constructions of material. For example, the term "layer" may include a portion, region, or other structure of material which is positioned proximate to another portion, region, or structure of differing material. For instance, a peg or similar structure may define a first "layer" of material, whereas a bearing body having a hole defined therein into which the peg is molded may define a second "layer" of material. Similarly, a flange secured around the periphery of a bearing body may define a first "layer" material, whereas the bearing body itself defines the second "layer" of material.

A polymer is preferably utilized in the construction of the layers 32, 34. As used herein, the term "polymer" is intended to mean any medical grade polymeric material which may be implanted into a patient. A specific example of such a polymer is medical grade polyethylene. The term "polyethylene", as defined herein, includes polyethylene, such as a polyethylene homopolymer, high density polyethylene, high molecular weight polyethylene, high density high molecular weight polyethylene, ultrahigh molecular weight polyethylene, or any other type of polyethylene utilized in the construction of a prosthetic implant. A more specific example of such a polymer is medical grade UHMWPE. The term "polymer" is also intended to include both homopolymers and copolymers; thus, "polymer" includes a copolymer comprising ethylene and acrylate, such as methyl methacrylate, methyl acrylate, ethyl methacrylate, ethyl acrylate and butyl methacrylate. The term "polymer" also includes oriented materials, such as the materials disclosed in pending U.S. patent application Ser. No. 09/961,842 entitled "Oriented, Cross-Linked UHMWPE Molding for Orthopaedic Applications", which was filed on Sep. 24, 2001 by King et al., which is hereby incorporated by reference, and which is owned by the same assignee as the present application.

The term "polymer" is also intended to include high temperature engineering polymers. Such polymers include members of the polyaryletherketone family and the polyimide family. Specific members of the polyaryletherketone family include polyetheretherketone, polyetherketone, and polyetherketoneetherketoneketone.

In one exemplary embodiment, a composite 30 is utilized in which the first polymer layer 32 of the composite 30 is constructed with a crosslinked polymer, whereas the second polymer layer 34 of the composite 30 is constructed with a non-crosslinked polymer. In a more specific exemplary embodiment, the polymer utilized in the construction of both the first polymer layer 32 and the second polymer layer 34 of the composite 30 is polyethylene. One particularly useful polyethylene for use in the construction of the first polymer layer 32 and the second polymer layer 34 of the composite 30 is UHMWPE.

As described above, a polymer may be crosslinked by, for example, exposure to radiation such as gamma radiation. As such, the first polymer layer 32 (i.e., the crosslinked polymer layer) of the composite 30 of this exemplary embodiment may be fabricated by exposing the first polymer layer 32 to gamma radiation. Such exposure may be in the exemplary range of 10-150 KGy. The second polymer layer 34 (i.e., the non-crosslinked polymer layer) of the composite 30 of this exemplary embodiment is not exposed to such gamma radiation. As a result, a composite 30 constructed in accordance with this exemplary embodiment provides for an articulating surface 18 constructed of a crosslinked polymer, along with an engaging surface 20 constructed of non-crosslinked polymer. In a more specific exemplary embodiment, the first polymer layer 32 (and hence the articulating surface 18 formed therein) is constructed of a crosslinked polyethylene such as crosslinked UHMWPE, whereas the second polymer layer 34 (and hence the engaging surface 20 formed therein) is constructed of a non-crosslinked polyethylene such as a non-crosslinked UHMWPE.

Such a composite structure provides a number of advantages to the design of the prosthetic bearing 10. For example, as described above, use of a crosslinked polymer such as a crosslinked polyethylene (e.g., crosslinked UHMWPE) enhances certain favorable mechanical characteristics relating to the articulating surface 18 (e.g., high wear resistance and high oxidation resistance). Moreover, use of non-crosslinked polymers such as a non-crosslinked polyethylene (e.g., non-crosslinked UHMWPE) enhances the mechanical characteristics relating to the locking or engagement of the bearing 10 to another component or to the bone itself (e.g. enhanced ductility, toughness, creep resistance). As such, a prosthetic bearing 10 constructed in accordance with this exemplary embodiment has an articulating surface 18 which possesses the favorable mechanical characteristics associated with crosslinked polymers, along with an engaging surface 20 (and associated features such as pegs, pins, posts, etcetera) which possesses the favorable mechanical characteristics associated with non-crosslinked polymers.

In another exemplary embodiment, a composite 30 is utilized in which the first polymer layer 32 of the composite 30 is constructed from a polymer which has been crosslinked to a first degree, whereas the second polymer layer 34 of the composite 30 is constructed from a polymer which has been crosslinked to a second degree. Specifically, the second polymer layer 34 is constructed of a polymer which has been crosslinked to a lesser degree than the polymer utilized in the construction of the first polymer layer 32. One way to vary the degree in which a polymer is crosslinked is to vary the dose of radiation to which it is exposed. Specifically, in a general sense, the greater the dose of radiation to which the polymer is exposed, the greater the degree in which the polymer is crosslinked. As such, in regard to the composite 30 of this exemplary embodiment, the first polymer layer 32 is exposed to a first dose of gamma radiation, whereas the second polymer layer 34 is exposed to a second, different dose of gamma radiation. In a more specific exemplary embodiment, the dose of gamma radiation to which the second polymer layer 34 is exposed is less than the dose of radiation to which the first polymer layer 32 is exposed.

Hence, in a specific implementation of the composite 30 of this exemplary embodiment, the first polymer layer 32 may be constructed from a polyethylene such as UHMWPE which has been exposed to a first dose of gamma radiation. The second polymer layer 34, on the other hand, may be constructed with a polyethylene such as UHMWPE which has been exposed to a second, different dose of gamma radiation. It should be appreciated that the dose of gamma radiation to which the polyethylene of the second polymer layer 34 is exposed is less than the dose of radiation to which the polyethylene of the first polymer layer 32 is exposed.

It should be appreciated that the second polymer layer 34 of this exemplary composite 30, although crosslinked to some degree, still possesses many of the previously described favorable mechanical characteristics relating to a non-crosslinked polymer (e.g., enhanced ductility, toughness, and creep resistance) relative to polymers crosslinked to the same degree as the first polymer layer 32. Specifically, by crosslinking the second polymer layer 34 to a lesser degree than the first polymer layer 32, the second polymer layer 34 is able to retain more of the favorable properties relating to the engaging surface 20 relative to the properties it would possess if crosslinked to the same degree as the first polymer layer 32.

As alluded to above, the material from which the second polymer layer 34 is constructed may be selected based on whether the bearing 10 is utilized in conjunction with another implanted prosthetic component or secured directly to the bone (e.g., by use of bone cement). For example, the above described use of a polyethylene (e.g., UHMWPE) in the construction of the second polymer layer 34 (albeit non-crosslinked or crosslinked to a lesser degree than the first polymer layer 32) is particularly useful in regard to the design of bearings 10 which are utilized in conjunction with an implanted shell or tray component. However, in regard to the design of bearings 10 which are secured directly to the bone, other types of materials may be desirable in order to increase the adhesion of the bearing 10 to bone cement.

For example, in another exemplary embodiment, the second polymer layer 34 may be constructed of a copolymer which provides for adhesion to both the polymer associated with the first polymer layer 32 and bone cement. For instance, in the case of when a polymer such as polyethylene is utilized in the construction of the first polymer layer 32, a copolymer comprising ethylene and an acrylate may be utilized. It should be appreciated that, as used herein, the term "acrylate" when utilized generally (as opposed to when used in regard to the name of a specific compound or monomer) is intended to mean any compound possessing an $\alpha,\beta$-unsaturated (i.e., 2-unsaturated) ester moiety. Examples of such $\alpha,\beta$-unsaturated esters include methyl acrylate, ethyl acrylate, methyl methacrylate, ethyl methacrylate, butyl methacrylate, and the like.

Use of such an ethylene-acrylate copolymer provides a number of advantages. Firstly, the ethylene portion of the copolymer is particularly well suited for adhering to the polymer (e.g., polyethylene) of the first polymer layer 32 during fusion of the first polymer layer 32 and the second polymer layer 34 to one another. On the other hand, the acrylate portion of the copolymer is particularly well suited for adhesion to bone cement such as bone cement that includes poly methyl methacrylate (PMMA). In an exemplary embodiment, the ethylene-acrylate copolymer is 5-60% acrylate on a molar basis. In a more specific exemplary embodiment, the ethylene-acrylate copolymer is 15-35% acrylate on a molar basis.

In a specific exemplary embodiment, an ethylene-methyl methacrylate copolymer may be utilized in the construction of the second polymer layer 34. In another specific exemplary embodiment, an ethylene-methyl acrylate copolymer may be utilized in the construction of the second polymer layer 34. In a further specific exemplary embodiment, an ethylene-ethyl acrylate copolymer may be utilized in the construction of the second polymer layer 34. Moreover, in another specific exemplary embodiment, an ethylene-butyl methacrylate copolymer may be utilized in the construction of the second polymer layer 34.

As indicated above, the composite prosthetic bearing 10 may also be designed to be press fit to another implanted prosthetic bearing component. For such a press-fit application, the second layer of polymer 34 may include a material with properties desirable for such an application. For example, the second layer of polymer 34 may include an UMWPE, an ethylene homopolymer or an ethylene copolymer. However, it should be understood that the invention is not limited to a particular polymer material for the second layer of polymer 34, and may encompass newly developed materials with properties desirable for the application, unless the claims expressly call for a particular material.

Moreover, it should also be appreciated that the aforedescribed ethylene-acrylate copolymers for use in the construction of the second polymer layer 34 may be utilized in conjunction with any number of different types of polyethylene-based first polymer layers 32. For example, the first polymer layer 32 may be constructed of UHMWPE. As a further example, the crosslinked UHMWPE of either layer 32, 34 may be an oriented material such as the materials described in U.S. patent application Ser. No. 09/961,842. The first layer of polymer 32 may also comprise a crosslinked ethylene homopolymer. And although crosslinked polymers are believed at present to provide superior wear resistance and oxidation resistance for the articulating surface in orthopaedic implants, new materials may be developed in the future with improved properties. Accordingly, the present invention is not limited to any particular material, and may encompass newly developed materials, unless a particular material is expressly set forth in the claims. In one specific exemplary embodiment, a bearing 10 is constructed with a composite 30 having a first polymer layer 32 constructed with crosslinked UHMWPE, along with a second polymer layer 34 constructed with an ethylene-acrylate copolymer.

The laminar composites 30 of the present invention may be fabricated by any technique which produces the aforedescribed features. One exemplary manner for constructing the laminar composites 30 of the present invention is by use of compression molding techniques. For example, material from which the first polymer layer 32 is to be constructed is placed in a mold, along with material from which the second polymer layer 34 is to be constructed. Thereafter, the two materials are compression molded to one another under process parameters which cause the second material (i.e., the material from which the second polymer layer 34 is constructed) to be molten and fused to the first material thereby creating the composite 30. It should also be appreciated that the mold may be configured so as to not only fuse the two materials to one another, but also form the composite 30 into the predetermined shape associated with a prosthetic bearing 10 (e.g., the glenoid bearing 12, the acetabular bearing 14, or the tibial bearing 16). In essence, the compression molding process not only creates the laminar composite 30 (i.e., fuses the two materials to one another), but also forms the resulting composite 30 into the desired, predetermined shape of a bearing 10.

The starting materials (e.g., polymers such as polyethylene) for use in the molding process may be provided in a number of different forms. For example, each of the starting materials may be provided as a preform. What is meant herein by the term "preform" is an article that has been consolidated, such as by ram extrusion or compression molding of polymer resin particles, into rods, sheets, blocks, slabs, or the like. The term "preform" also includes a preform "puck" which may be prepared by intermediate machining of a commercially available preform. Polymer preforms such as polyethylene preforms may be provided in a number of different pre-treated or preconditioned variations. For example, crosslinked or non-crosslinked (e.g., irradiated or non-irradiated) preforms may be utilized. Such preforms may be quenched or non-quenched.

The starting materials (e.g., polymers and copolymers) may also be provided as powders. What is meant herein by the term "powder" is resin particles. Similarly to as described above in regard to preforms, powders may be provided in a number of different pre-treated or preconditioned variations. For example, crosslinked or non-crosslinked (e.g., irradiated or non-irradiated) powders may be utilized.

The starting materials (e.g., polymers and copolymers) may also be provided as porous structures. What is meant herein by the term "porous structure" is a structure of compacted resin particles. The porous structure may take many forms including blocks or pucks. However, unlike preforms, a porous structure is constructed of unfused or partially fused resin particles. The porous structure may be provided in varying degrees of porosity and may include crosslinked or non-crosslinked (e.g., irradiated or non-irradiated) resin particles. In the case of a porous structure that is crosslinked via irradiation, the resin particles are typically compacted together prior to exposure to gamma or other types of radiation. However, it should be appreciated that the resin particles may be irradiated prior to compaction, if desired.

It should be appreciated that the starting materials (e.g., the preforms, powders, or porous structures) may be "pre-irradiated", "pre-quenched", or otherwise preconditioned prior to use thereof. In particular, it may be desirable for a manufacturer of prosthetic bearings to purchase material (e.g. polyethylene) which has been irradiated (or otherwise crosslinked), pre-quenched, or otherwise preconditioned by a commercial supplier or other manufacturer of the material. Such "out-sourcing" of preconditioning processes is contemplated for use in the processes described herein.

In addition to the forms of starting materials described above, the starting material may be in the form of a sheet or film, particularly where the layer of polymer comprises a copolymer of ethylene and acrylate.

In regard to fabrication of a composite 30 in which the first polymer layer 32 is constructed of crosslinked polymer and the second polymer layer 34 is constructed of non-crosslinked polymer, a number of fabrication processes may be utilized. Firstly, a preform of crosslinked polymer (i.e., pre-irradiated) may be placed in a mold, along with a preform of polymer which is non-crosslinked (i.e., non-irradiated). Thereafter, the two preforms are compression molded to one another under process parameters which cause the non-crosslinked preform of polymer to be molten and fused to the preform of crosslinked polymer. It should also be appreciated that during such a molding process, the resultant composite 30 formed by the fusing of the two preforms to one another is contemporaneously formed into the predetermined shape associated with a prosthetic bearing 10 (e.g., the glenoid bearing 12, the acetabular bearing 14, or the tibial bearing 16). In an exemplary implementation of this process, a preform of a crosslinked polyethylene such as crosslinked UHMWPE is compression molded to a preform of a non-crosslinked polyethylene such as non-crosslinked UHMWPE.

Such a composite 30 (i.e., a first polymer layer 32 constructed of crosslinked polymer and a second polymer layer 34 constructed of non-crosslinked polymer) may also be fabricated by the use of polymer powders or porous structures. For example, a preform of crosslinked polymer (i.e., pre-irradiated) may be placed in a mold, along with polymer powder which is non-crosslinked (i.e., non-irradiated). Thereafter, the two materials are compression molded to one another under process parameters which cause the non-crosslinked polymer powder to be molten and fused to the preform of crosslinked polymer. The composite 30 formed by the fusing of the two materials (i.e., the crosslinked preform and the non-crosslinked powder) to one another may be contemporaneously formed into the predetermined shape associated with a prosthetic bearing 10 (e.g., the glenoid bearing 12, the acetabular bearing 14, or the tibial bearing 16). In an exemplary implementation of this process, the crosslinked preform may be provided as a crosslinked polyethylene preform such as a crosslinked UHMWPE preform, whereas the non-crosslinked powder may be provided as a non-crosslinked polyethylene powder such as a non-crosslinked UHMWPE powder.

Similarly, a porous structure of crosslinked polymer (i.e., pre-irradiated) may be placed in a mold, along with polymer powder which is non-crosslinked (i.e., non-irradiated). Thereafter, the two materials are compression molded to one another under process parameters which cause the non-crosslinked polymer powder to be molten and fused to the porous structure of crosslinked polymer. The composite 30 formed by the fusing of the two materials (i.e., the crosslinked porous structure and the non-crosslinked powder) to one another may be contemporaneously formed into the predetermined shape associated with a prosthetic bearing 10 (e.g., the glenoid bearing 12, the acetabular bearing 14, or the tibial bearing 16). In an exemplary implementation of this process, the crosslinked porous structure is provided as a crosslinked polyethylene porous structure such as a crosslinked UHMWPE porous structure, whereas the non-crosslinked powder is provided as a non-crosslinked polyethylene powder such as a non-crosslinked UHMWPE powder.

Moreover, a porous structure of crosslinked polymer (i.e., pre-irradiated) may be placed in a mold, along with a polymer preform which is non-crosslinked (i.e., non-irradiated). Thereafter, the two materials are compression molded to one another under process parameters which cause the non-crosslinked polymer preform to be molten and fused to the porous structure of crosslinked polymer. The composite 30 formed by the fusing of the two materials (i.e., the crosslinked porous structure and the non-crosslinked preform) to one another may be contemporaneously formed into the predetermined shape associated with a prosthetic bearing 10 (e.g., the glenoid bearing 12, the acetabular bearing 14, or the tibial bearing 16). In an exemplary implementation of this process, the crosslinked porous structure is provided as a crosslinked polyethylene porous structure such as a crosslinked UHMWPE porous structure, whereas the non-crosslinked preform is provided as a non-crosslinked polyethylene preform such as a non-crosslinked UHMWPE preform.

In regard to fabrication of a composite 30 in which the first polymer layer 32 is constructed of a polymer which has been crosslinked to a first degree and the second polymer layer 34 is constructed of a polymer which has been crosslinked to a second, lesser degree, a number of fabrication processes may also be utilized. Firstly, a preform of polymer crosslinked to a first degree may be placed in a mold, along with a preform of polymer which is crosslinked to a second, lesser degree. Thereafter, the two preforms are compression molded to one another under process parameters which cause the polymer of the second preform to be molten and fused to the polymer of the first preform. Similarly to as described above, the resultant composite 30 formed by the fusing of the two preforms to one another is contemporaneously formed into the predetermined shape associated with a prosthetic bearing 10 (e.g., the glenoid bearing 12, the acetabular bearing 14, or the tibial bearing 16). In an exemplary implementation of this process, a preform of polyethylene such as UHMWPE which is crosslinked to a first degree is compression molded to a preform of polyethylene such as UHMWPE which is crosslinked to a second, lesser degree.

Such a composite 30 (i.e., a first polymer layer 32 constructed of a polymer which has been crosslinked to a first degree and a second polymer layer 34 constructed of a polymer which has been crosslinked to a second, lesser degree) may also be fabricated by the use of polymer powders or porous structures. For example, a powder of polymer crosslinked to a first degree may be placed in a mold, along with a preform of polymer which is crosslinked to a second, lesser degree. Thereafter, the two materials (i.e., the powder and the preform) are compression molded to one another under process parameters which cause the polymer of the preform to be molten and fused with the polymer of the powder. Similarly to as described above, the resultant composite 30 formed by the fusing of the two materials to one another is contemporaneously formed into the predetermined shape associated with a prosthetic bearing 10 (e.g., the glenoid bearing 12, the acetabular bearing 14, or the tibial bearing 16). In an exemplary implementation of this process, a powder of polyethylene such as UHMWPE which is crosslinked to a first degree is compression molded to a preform of polyethylene such as UHMWPE which is crosslinked to a second, lesser degree.

It should be appreciated that the forms in which the two materials are provided may be swapped. Specifically, a preform of polymer crosslinked to a first degree may be compression molded with a powder of polymer which is crosslinked to a second, lesser degree in a similar manner to as described above.

Moreover, a powder of polymer crosslinked to a first degree may be placed in a mold, along with a porous structure of polymer which is crosslinked to a second, lesser degree. Thereafter, the two materials (i.e., the powder and the porous structure) are compression molded to one another under process parameters which cause the polymer of the porous structure to be molten and fused to the polymer of the powder. Similarly to as described above, the resultant composite 30 formed by the fusing of the two materials to one another is contemporaneously formed into the predetermined shape associated with a prosthetic bearing 10 (e.g., the glenoid bearing 12, the acetabular bearing 14, or the tibial bearing 16). In an exemplary implementation of this process, a powder of polyethylene such as UHMWPE which is crosslinked to a first degree is compression molded with a porous structure of polyethylene such as UHMWPE which is crosslinked to a second, lesser degree.

It should be appreciated that the forms in which the two materials are provided may be swapped. Specifically, a porous structure of polymer crosslinked to a first degree may be compression molded with a powder of polymer which is crosslinked to a second, lesser degree in a similar manner to as described above.

A similar fabrication process may be utilized in regard to fabrication of a composite 30 having a first polymer layer 32 constructed of a polymer (e.g., polyethylene) and a second polymer layer 34 constructed of an ethylene-acrylate copolymer. In particular, a polymer preform may be placed in a mold, along with a preform of an ethylene-acrylate copolymer. Thereafter, the two preforms are compression molded to one another under process parameters which cause the copolymer preform to be molten and fused to the polymer preform. Similarly to as described above, the resultant composite 30 formed by the fusing of the two preforms to one another is contemporaneously formed into the predetermined shape associated with a prosthetic bearing 10 (e.g., the glenoid bearing 12, the acetabular bearing 14, or the tibial bearing 16). In an exemplary implementation of this process, the polymer preform is provided as a polyethylene preform such as a UHMWPE preform (crosslinked or non-crosslinked, quenched or non-quenched), whereas the copolymer preform is provided as a PMMA compatible preform.

It should be appreciated that other starting material forms may also be utilized in the fabrication of a composite 30 in which the first polymer layer 32 is constructed of a polymer (e.g., polyethylene) and the second polymer layer 34 is constructed of an ethylene-acrylate copolymer. For example, in addition to preforms, the polymer utilized in the construction of the polymer layer 32 may be provided as either powders or porous structures. Likewise, in addition to preforms, the copolymer utilized in the construction of the polymer layer 34 may be provided as either powders or porous structures.

It should also be appreciated that although the composites 30 have herein been described as having two layers, and have significant advantages thereby in the present invention, other composite configurations are also contemplated. For example, the composite 30 may be configured to include several alternating layers of materials similar to the materials used in regard to the two-layer composites described above. For instance, the composite 30 may be configured to include several (i.e., more than two) layers of alternating crosslinked and non-crosslinked UHMWPE.

Moreover, it may be desirable to use vacuum molding for some materials. For example, vacuum molding may be preferred where one or more of the layers comprises a non-quenched material.

Advantageously, the tensile properties associated with the interfaces between the layers 32, 34 are as strong as at least the weaker of the individual layers 32,34. Such interfacial tensile properties may be evaluated in an interfacial tensile test as a gauge for composite structure integrity. Type V tensile specimens of 400 micron thickness were prepared from various composites and were tested based on the ASTM D638 standard. The interface section was placed within the gauge length of the narrow section of the tensile test specimen.

TABLE I

Interfacial tensile properties of two examples of Crosslinked UHMWPE Composite Molding

| Composite Structure | Composition | Ultimate Tensile Strength, ksi | Elongation, % |
|---|---|---|---|
| Preform I- Preform II | Non-Irradiated GUR 1020 Preform- 50 KGy, Annealed GUR 1050 Preform | 8.12 +/− 0.95 | 397 +/− 55 |
| Powder- Preform | GUR 1020 Powder- 50 KGy, Annealed GUR 1050 Preform | 6.89 +/− 0.25 | 403 +/− 16 |

TABLE II

Tensile properties of pre-consolidated UHMWPE material

| Material | Ultimate Tensile Strength, ksi | Elongation, % |
|---|---|---|
| 50 KGy, Annealed GUR 1050, Ram Extruded | 7.56 +/− 0.49 | 301 +/− 23 |
| Non-Irraidated GUR 1020, Ram Extruded | 8.99 +/− 0.66 | 475 +/− 26 |

As shown in Tables I and II, interfacial ultimate tensile strength data indicate that the interfaces of composites 30 have an integrity which is approximately comparable to the fully consolidated or fully fused forms of the starting materials (i.e. the materials of which the individual layers 32, 34 are constructed). Moreover, the corresponding data for elongation at break at the interfaces for the composites 30 are at least as good as the weaker of the two starting materials.

In the composite structures of Table I, the two polymer layers 32, 34 have been fused by heating the two layers to cause the adjacent portions of both polymer layers to become molten while compression molding the layers into the composite. It should also be understood that other processes can be used to create such a melt-fused interface between the polymer layers. For example, welding can be used to create a melt-fused interface. It is believed that with melt-fusion, the polymer chains from each polymer layer become intermingled and entangled to create the strong interface, with strong bonding between the layers. Generally, the expressions "melt-fusion" and "melt-fused" are used herein to denote interfaces between polymer layers wherein the parts of both polymer layers at the interface have been melted.

It is expected that other methods of securing the two polymer layers can be used for some applications. For example, instead of melt-fusion, it is expected that mechanical interlocks can be used in some applications. With the choice of appropriate materials and processes, mechanical interlocks between polymer layers may provide an interface with adequate mechanical and dynamic properties for the composite to be used as an implantable bearing for an orthopaedic prosthesis.

For an application relying upon mechanical interlocks, it is anticipated that mechanical interlocking with adequate interfacial strength can be achieved by providing a second layer of polymer 34 comprising a porous structure of a high-temperature engineering polymer, such as one from the polyaryletherketone family or the polyimide family, and by control of process parameters. In such an application, a crosslinked UHMWPE layer may be used for the first layer of polymer 32 for the articulating surface. The crosslinked UHMWPE layer 32, in the form of a powder or preform, may be compression molded to the layer 34 of porous high temperature engineering polymer under a temperature that will melt at least a portion of the UHMWPE layer, so that UHMWPE melts into and fills some of the pores of the high temperature engineering material; when this UHMWPE material solidifies, the two polymer layers will be mechanically bonded together.

The compression molding can be done at a temperature high enough to melt the UHMWPE layer but below the melting point of the second layer of polymer 34. The high temperature may be localized at the interface of the layers 32, 34. The porous structure may comprise a solid section for machining into the final geometry. The structural integrity of the interface in this composite embodiment relies on mechanical interlocking of the two polymer layers. It is also anticipated that various mechanical locking mechanisms can be used, provided that materials and process parameters are selected to provide the desired strength at the interface of the polymer layers 32, 34.

The layer of porous high temperature engineering polymer may comprise a engineering polymer such as polyetheretherketone, polyetherketone, polyetherketoneetherketoneketone or polyimide. These materials are biocompatible and are able to withstand the processing temperature for UHMWPE without significant deformation. Required preform or porous structures can be readily fabricated from these raw materials using conventional processing techniques. Although it is expected that these polymer materials will be useful as one of the polymer layers when relying upon a mechanical interlock, the present invention is not limited to these materials unless the claims expressly call for them. The present invention may also encompass newly developed polymers, unless a particular polymer is expressly set forth in the claims.

In addition, although the mechanical interlock that secures the two polymer layers together can be formed by compression molding the two polymer layers together, methods such as hot isostatic pressing may be used to secure the two layers of polymer 32, 34 together with a mechanical interlock. In addition, as new polymer materials are developed, new methods of securing the polymer layers together may also be developed. Accordingly, the present invention is not limited to any particular means of securing the polymer layers together, and may encompass newly developed materials and securing means, unless a particular material or process is expressly set forth in the claims.

In addition to ultimate tensile strength and elongation, the interface of the two secured polymer layers in the composite bearing is expected to also have other mechanical and dynamic properties comparable to the other mechanical properties of at least the weaker of the fully fused or fully consolidated forms of the polymer material in the two layers. Mechanical and dynamic properties of the interface include not only ultimate tensile strength, yield strength, elongation to break, and modulus, but also oxidation resistance, impact strength, compression strength, shear strength and fatigue strength (as shown through different forms of fatigue testing, e.g., three-point bending, tension, compression and flex fatigue). "Comparable" is meant to include no statistical difference in properties, as well as overlaps in data points, as in the case of the ultimeate tensile strength of the Powder-Preform Composite Structure of Table I and the 50 KGy, Annealed GUR 1050 Ram Extruded material in Table II, for example.

It should be understood that unless specific mechanical and dynamic properties are expressly called for in the claims, the invention is not intended to be limited to composites with interfaces with any particular mechanical or dynamic property. Although the composite article should have properties suitable for an orthopaedic implant, the properties at the interface may not need to be comparable to the mechanical and dynamic properties of the fully consolidated materials of the layers. For example, if the two polymer layers are made of materials with great enough shear strength, then the shear strength of the interface may be less significant.

The composite articles with layers secured through a melt-fusion process possess may be preferred over those with layers secured through mechanical interlocks. The temperature of the melt-fusion process should be sufficient to destroy any contaminants at the pre-fusion interface. In addition, melt-fusion results in an interface where the two polymers are in intimate contact, with no pore, void, gap, crack or separation that would allow for the ingress of agents that would compromise sterilization. Therefore, surface sterilization should be adequate for the melt-fused polymer composite implants. The ability to use surface sterilization techniques, such as gas plasma sterilization and ethylene oxide sterilization, instead of irradiation, is advantageous when an UHMWPE material is used as one of the polymer layers. Gamma irradiation sterilization of UHMWPE material can generate free-radicals and can make the material more susceptible to oxidation.

For polymer composite bearings with polymer layers secured through mechanical interlocks, some gap or separation may continue to exist between the layers after they are secured together, since only one of the polymer layers will be melted. If the gap or separation is large enough, agents that could compromise sterilization could enter the gap. Accordingly, unless special processing techniques are employed, sterilization could require gamma irradiation to reach the level of the interface of the polymer layers. In addition, if either polymer layer exists as a porous structure after the polymer layers are secured together, proper sterilization will probably require gamma irradiation.

If it is desired to avoid gamma irradiation sterilization of composites with mechanical interlocks, known special processing techniques may be employed to ensure a sterile environment, such as processing in a clean room.

In addition, new sterilization techniques may be developed, and new materials may be developed, or materials may be selected that do not degrade under gamma irradiation sterilization. In either event, mechanical interlocking polymer layers may be preferred.

In addition to the ability to surface sterilize the melt-fused composite bearings of the present invention, the prosthetic bearings 10 and associated methods for making the same have a number of advantages over heretofore designed bearings and associated methods. For example, by constructing the bearing as a composite (i.e., the composite 30), the materials selected with each layer of the composite may be selected to provide the desired mechanical and dynamic properties. In particular, as described above, the layer in which the articulating surface 18 of the bearing 10 is defined may be constructed with materials which have favorable mechanical and dynamic properties for use as an articulating surface (e.g., high wear and oxidation resistance). On the other hand, the layer in which the engaging surface 20 is defined may be constructed with materials which have favorable mechanical and dynamic properties for use as an engaging surface (e.g., high ductility, toughness and creep resistance).

Moreover, use of an ethylene-acrylate copolymer as an underlying layer provides the bearings 10 of the present invention with advantages over heretofore designed composite bearings. Firstly, such a copolymer has a component for both (1) providing suitable adhesion to the polyethylene-based upper layer, and (2) providing suitable adhesion to bone cement. Other attempts at providing this functionality have been met with limited success since, amongst other things, they have attempted to utilize dry blends of materials (as opposed to an actual copolymer), and, as a result, have been subjected to both process and product variations.

While the invention has been illustrated and described in detail in the drawings and foregoing description, such an illustration and description is to be considered as exemplary and not restrictive in character, it being understood that only the illustrative embodiments have been shown and described and that all changes and modifications that come within the spirit of the invention are desired to be protected.

There are a plurality of advantages of the present invention arising from the various features of the prosthetic bearing described herein. It will be noted that alternative embodiments of each of the prosthetic bearings of the present invention may not include all of the features described yet benefit from at least some of the advantages of such features. Those of ordinary skill in the art may readily devise their own implementations of prosthetic bearings that incorporate one or more of the features of the present invention and fall within the spirit and scope of the present invention as defined by the appended claims.

For example, although it has been described herein to crosslink materials via irradiation, a process which has numerous advantages in regard to the present invention, it should be appreciated that certain of such advantages may be achieved by crosslinking the materials by any suitable technique. In addition, although the crosslinked polymer or more highly crosslinked polymer may typically be used for the articulating surface of the composite with non-crosslinked or less crosslinked polymer being used for the engaging surface, there may be instances where it is desirable for the crosslinked polymer or more highly crosslinked polymer layer to be used for the engaging surface and the non-crosslinked or less crosslinked polymer to be used for the articulating surface.

What is claimed is:

1. An implantable orthopaedic prosthesis, comprising:
a laminar composite bearing having (i) a radiation crosslinked, quenched layer of polyethylene having an articulating surface defined in a first side thereof; and (ii) a non-crosslinked layer of polyethylene molded to a second, opposite side of said crosslinked, quenched layer of polyethylene at a melt fused interface, wherein non-crosslinked polyethylene of the non-crosslinked layer of polyethylene is fused to crosslinked, quenched polyethylene of the crosslinked layer of polyethylene at the melt-fused interface.

2. The implantable orthopaedic prosthesis of claim 1, wherein said radiation crosslinked, quenched layer of polyethylene and said non-crosslinked layer of polyethylene are compression molded to one another.

3. The implantable orthopaedic prosthesis of claim 1, wherein:
said non-crosslinked layer of polyethylene has an engaging surface defined therein which is adapted to be secured to an acetabulum of a patient.

4. The implantable bearing of claim 1, wherein:
said crosslinked layer of polymer has an articulating surface defined therein, and
said non-crosslinked layer of polymer has an engaging surface defined therein which is adapted to be secured to a glenoid of a patient.

5. The implantable bearing of claim 1, wherein:
said crosslinked layer of polymer has an articulating surface defined therein, and
said non-crosslinked layer of polymer has an engaging surface defined therein which is adapted to be secured to a tibia of a patient.

6. The implantable orthopaedic prosthesis of claim 1, wherein said radiation crosslinked, quenched layer of polyethylene comprises a radiation crosslinked, annealed layer of polyethylene.

7. An implantable orthopaedic prosthesis, comprising:
a laminar composite bearing having (i) a first layer of polyethylene having an articulating surface defined in a first side thereof; and (ii) a second layer of polyethylene molded to a second, opposite side of said first layer of polyethylene at a melt-fused interface, wherein (a) said first layer of polyethylene is radiation crosslinked to a first degree and quenched (b) said second layer of polyethylene is radiation crosslinked to a second degree that is different than said first degree and quenched, and (c) polyethylene crosslinked to the second degree of the second layer of polyethylene is fused to polyethylene crosslinked to the first degree of the first layer of polyethylene at the melt-fused interface.

8. The implantable orthopaedic prosthesis of claim 7, wherein said second degree is less than said first degree.

9. The implantable orthopaedic prosthesis of claim 7, wherein said first layer of polyethylene and said second layer of polyethylene are compression molded to one another.

10. The implantable orthopaedic prosthesis of claim 7, wherein:
said second layer of polyethylene has an engaging surface defined therein which is adapted to be secured to an acetabulum of a patient.

11. The implantable bearing of claim 7, wherein:
said first layer of polyethylene has an articulating surface defined therein, and
said second layer of polyethylene has an engaging surface defined therein which is adapted to be secured to a glenoid of a patient.

12. The implantable bearing of claim 7, wherein:
said first layer of polyethylene has an articulating surface defined therein, and
said second layer of polyethylene has an engaging surface defined therein which is adapted to be implanted into a tibia of a patient.

13. The implantable orthopaedic prosthesis of claim 7, wherein said first layer of polyethylene and said second layer of polyethylene comprise crosslinked, annealed polyethylene.

* * * * *